United States Patent [19]
Anderson et al.

[11] Patent Number: 5,695,738
[45] Date of Patent: Dec. 9, 1997

[54] STEROIDAL C-GLYCOSIDES

[75] Inventors: Mark Anderson, Orinda; John Henry Musser, San Carlos, both of Calif.

[73] Assignee: Glycomed Incorporated, Alameda, Calif.

[21] Appl. No.: 490,965

[22] Filed: Jun. 15, 1995

[51] Int. Cl.$^6$ .................. A61K 31/70; A61K 51/00; C07J 9/00
[52] U.S. Cl. .................. 424/1.73; 424/9.1; 514/25; 514/359; 514/461; 536/5; 536/6; 536/6.1; 536/6.2; 540/94; 540/95; 540/97
[58] Field of Search .................. 536/5, 6, 6.1, 6.2; 574/25; 424/1.73, 9.1; 540/94, 95, 97; 514/359, 461

[56] References Cited

U.S. PATENT DOCUMENTS

| | | | |
|---|---|---|---|
| 4,189,471 | 2/1980 | Ponpipom et al. | 424/88 |
| 4,229,441 | 10/1980 | Bugianesi et al. | 424/182 |
| 4,259,324 | 3/1981 | Ponpipom et al. | 424/180 |
| 4,562,250 | 12/1985 | Staba et al. | 536/6 |
| 4,652,637 | 3/1987 | Hagmann et al. | 536/5 |

FOREIGN PATENT DOCUMENTS

| | | |
|---|---|---|
| 9305790 | 4/1993 | WIPO . |
| 9411030 | 5/1994 | WIPO . |

OTHER PUBLICATIONS

John C. Chabala and Tsung Y. Shen, "The Preparation of 3–Cholesteryl 6–(Glycosylthio)Hexyl Ethers and Their Incorporation into Liposomes", *Carbohydrate Research*, 67 (1978) 55–63.

Mitree M. Ponpipom, Robert L. Bugianesi, Tsung–Ying Shen, "Glycolipids as Potential Immunologic Adjuvants", *J. Med. Chem.*, (1980) 23:1184–88.

M.M. Ponpipom, R.L. Bugianesi, and T.Y. Shen, "Cell Surface Carbohydrates for Targeting Studies", *Can. J. Chem.*, (1980) 58:214.

Maarten H.D. Postema, "Recent Developments Int He Synthesis of C–Glyosides", *Tetrahedron*, vol. 48, No. 40, pp.8545–8599, 1992.

Primary Examiner—Elli Peselev
Attorney, Agent, or Firm—Lyon & Lyon LLP

[57] ABSTRACT

Compositions of sterodial glycosides are described wherein the glycoside is linked directly, or indirectly to a desired steroidal compound via a carbon, or similar stable linkage, and methods of using the compositions to treat patients by binding to and/or blocking cellular receptors for a variety of diseases including cancer, inflammation, and autoimmune diseases.

15 Claims, No Drawings

STEROIDAL C-GLYCOSIDES

FIELD OF THE INVENTION

The invention relates to the field of medicinal chemistry, and more specifically to steroidal glycosides wherein the glycoside is linked directly, or indirectly to a desired steroidal compound via a carbon linkage, to formulations containing such, and their use in treating patients suffering from a variety of diseases including cancer, inflammation, and autoimmune diseases.

BACKGROUND OF THE INVENTION

Certain steroidal glycosides are known to have particular medical applications. Noteworthy is U.S. Pat. No. 4,652,637 which shows steroidal glycosides, in which steroids are bridged via a medium length hydrocarbon chain to 1-thio-D-mannopyranoses or 1-thio-L-fucopyranoses. The compounds are described as being useful immunological adjuvants. See also, U.S. Pat. No. 4,259,324; U.S. Pat. No. 4,229,441; U.S. Pat. No. 4,189,471; and Carbohydrate Res. 67, 55–63 (1978) by J. C. Chabala and T. Y. Shen; and J Med. Chem. 23, pp. 1184–1188 by M. M. Ponpipom et al.; and Can, J. Chem. 58,pp. 214–220 (1980) by M. M. Poniopom et al. Also noteworthy is patent application W09305790-A1 which describes 14-aminosteroidal glycosides that are particularly useful for treating severe congestive heart failure. The aforementioned steroidal glycosides have the glycoside moiety linked via an oxygen atom to the steroid. Such O-linkages are unstable when administered to a patient since the O-linkage is susceptible to degradation by enzymes in bodily fluids or tissues.

There is a continuing need for safe and effective drugs that can be used to prevent or treat disease, and particularly to treat the inflammatory response often associated with certain diseases.

To date, there have been few reports showing significant efficacy of steroidal glycosides for the treatment of inflammation. It is known that for an acute inflammatory response to occur, circulating leukocytes must bind to and penetrate the vascular wall and access the site of injury. A large body of data has been accumulated that implicates a family of receptors, the selectins (or Lectin, EGF, Complement-Cellular Adhesion Molecules) (hereinafter LEC-CAMs), in many of the initial interactions between leukocytes and vascular endothelia. The three known members of this family, L-Selectin (LECAM-1, LAM-1, gp90MEL), E-Selectin (LECAM-2, ELAM-1)and P-Selectin (LECAM-3, GMP-140, PADGEM), each contain a domain with homology to the calcium-dependent lectins (C-lectins), an EGF-like domain, and several complement binding protein-like domains (Bevilacqua et el., Science (1989) 243:1160–1165; Johnston et el., Cell (1989) 56:1033–1044; Lasky et el., Cell (1989) 56:1045–1055; Tedder et el., J. Exp. Med. (1989) 170:123–133). Thus, one mechanism whereby anti-inflammatory drugs could exert their effect would be to interfere with leuckocyte binding to, and penetration through the vascular wall.

The present invention avoids and overcomes the obstacles inherent in varying steroid glycosides as drugs, that is the instability of the O-glycosidic bond, by employing carbon glycosidic bonds for the attachment of glycosides to steroids. Such compounds have utility in the treatment or prevention of certain diseases including inflammation.

A carbon-glycoside bond results when the oxygen of the anomeric carbon of a glycoside is replaced by a carbon atom. For example, when the oxygen linkage in a disaccharide is replaced by a methylene group, a carbon glycoside is formed. Such carbon glycoside is no longer cleavable by hydrolysis and tends to be enzymatically stable. Carbon glycosides have been used for enzymetic and metabolic studies. See, Lalegerie et al., 1982, Biochemie 64:977; Shulman et al., 1974, Carbohydr. Res. 33:229; Chmielewski et al., 1981, ibid. 97. Carbon glycosides have been developed as breast cancer chemopreventive drugs (PCT Patent Application, WO 94/11030, published May, 1994).

SUMMARY OF THE INVENTION

The present invention relates to the field of steroidal chemistry and is directed to tools and methods for the generation of chemical compounds consisting of at least one carbohydrate unit and asteroid. One aspect of the invention is to provide "activated" carbon glycosides/heteroatom glycosides useful as tools for the incorporation of carbohydrate units into steroids comprising suitable functional groups. The "activated" carbon glycosides/heteroatom glycosides compounds provided by the present invention comprise the following general formulae:

$(X)_m-Z$ wherein:

X is a carbohydrate unit or modified carbohydrate unit;

Z is an activated functional group attached to an X at the anomeric position which is carbon m is a positive integer;

with the proviso that at least one X does not have an oxygen at its anomeric position.

In a more specific embodiment, the activated carbon glycoside/heteroatom glycoside $[(X)_m-Z]$ provided by the present invention is further defined as a compound comprising the following formula:

$[(X)_m-Z]=$

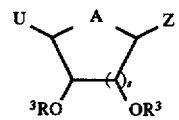

and pharmaceutically acceptable salts thereof, wherein:

Z is —$CH_2WCH_2T$, —C≡$CCH_2T$, =C=$CHCH_2T$, —$ArCH_2T$, —$(CH_2)_nV$;

W is C=O, C=$CR^1_2$, $CR^1CR^1_3$, $CR^1$—$CR^1_2OR^1$, $COR^1$—$CR^1_2OR^1$, $CR^1_2$, $CR^2$—$CR^2_2OR^3$, $CR^2$—$CR^2R^1_2$;

T is $O^-M^1$, $M^2$, $SR^1$, $S(O)R^1$, $SO_2R^1$, $P(O)OR^1_2$, COD, O—$C(NH)CCl_3$, $NR^1_2$;

V is $O^{-M1}$, $SR^1$, $S(O)R^1$, $SO_2R^1$, $P(O)OR^1_2$, COD, $NR^1_2$;

n is a positive integer;

$M^1$ is $Na^+$, $K^+$, $Mg^{++}$, or $Ca^{++}$ ions;

$M^2$ is $Li^+$, $Mg^{++}$, $Ca^{++}$, $Cu^{++}$, $Cu^+$, ions;

$R^1$ is H, $CH_3$, lower alkyl;

$R^2$ is $OR^1$, $NR^1_2$, $SR^1$;

$R^3$ is $R^1$, protecting group, $SO_3M^1$, O-carbohydrate (linear or branched);

s is 1, 2, 3;

Protecting Groups include lower methyl-, benzyl-, MOM, MEM, MPM, tBDMS;

U is $CH_2OR^1$, $CH_2O$-protecting group, $CH_2OSO_3M^1$, $CH_2SO_3M^1$, $CH_2OR^3$, COD;

A is O, S, $NR^1_2CR^1_2$, $NR^1$;

D is $OR^1$, $NR^1{}_2$, $O^-M^1$;

Lower Alkyl is $C_1$ to $C_{10}$, branched or unbranched.

or:

Z is $CH_2-W-CH_2E$, $-C\equiv CCH_2E$, $=C=CHCH_2E$, $-ArCH_2E$, $-(CH_2)_nG$

W is $C=O$, $C=CR^1{}_2$, $CR^1CR^1{}_3$, $CR^1-CR^1{}_2OR^1$, $COR^1-CR^1{}_2OR^1$, $CR^1{}_2$, $CR^2-CR^2{}_2OR^3$, $CR^2-CR^2R^1{}_2$;

E is Cl, Br, I, OMs, OTf, OTs, OAc, O—C(NH)CCl$_3$;

G is Cl, Br, I, OMs, OTf, OTs, OAc, COD;

n is a positive integer;

$M^1$ is $Na^+$, $K^+$, $Mg^{++}$, or $Ca^{++}$ ions;

$R^1$ is H, lower alkyl;

$R^2$ is $OR^1$, $NR^1{}_2$, $SR^1$;

$R^3$ is $R^1$, protecting group, $SO_3M^1$, O-carbohydrate (linear or branched);

s is 1, 2, 3;

Protecting Groups include lower methyl-, benzyl-, benzoyl-, acetyl-, MOM, MEM, MPM, tBDMS, TMS;

U is $CH_2OR^1$, $CH_2O$-protecting group, $CH_2OSO_3M^1$, $CH_2SO_3M^1$, $CH_2OR^3$, COD;

A is O, S, $NR^1{}_2CR^1{}_2$, $NR^1$;

D is $OR^1$, $NR^1{}_2$, $O^-M^1$;

Lower Alkyl is $C_1$ to $C_{10}$, branched or unbranched.

Another aspect of the present invention is to provide methods for preparing modified steroids comprising a plurality of compounds wherein each compound is composed of one or a plurality of at least one monomer which is a modified carbohydrate. More specifically, the methods provide reacting (X)m–Z, in a Z-primed reaction, with steroidal compounds to yield a product having the steroid bound to (X)m and generally denoted as (X)mZ'.

The compounds generated by the methods of the present invention may comprise an array of molecules with a diverse steroidal core structure, a diverse carbohydrate moiety or both. The carbohydrate moieties employed for the generation of such compounds include monomers, dimers, trimers, oligomers, branched or unbranched, linked to a suitable functional group of a chemical moiety comprising such functional group. Suitable functional groups include, but are not limited to, hydroxyl, carboxyl, thiol, amido, and amino groups.

In the case in which a moiety has more than one such suitable functional group, one or more such functional groups may be protected by suitable protecting groups during the coupling reaction. Such protecting groups include, but are not limited to, benzyl, or alkyl groups. After the coupling reaction, the protecting groups may selectively be removed.

The plurality of different steroidal members may be synthesized either in liquid phase or, alternately, linked to a solid synthesis support or in a mixture of both. After synthesis, the steroidal members may be cleaved from the synthesis support.

Still another aspect of the invention is to provide an array of novel steroidal chemical compounds comprising at least one carbohydrate unit, including a carbon glycoside/heteroatom glycoside, linked to a suitable derivatized functional group. The subject invention provides novel steroidal chemical compounds comprising the formula:

$(X)_m-Z'$ wherein:

X is a carbohydrate unit or modified carbohydrate unit;

Z' is the reaction product of "Z" and asteroid, where Z is an activated functional group attached to a X at the anomeric position which is carbon;

m is a positive integer; with the proviso that at least one X does not have an oxygen at its anomeric position.

DETAILED DESCRIPTION OF THE INVENTION

The present invention relates to the field of steroidal chemistry. Specifically, the invention is directed to tools and methods for generating novel steroidal compounds comprising at least one carbohydrate unit. The present invention is based, in part, on the novel use of carbon glycosides as modifiers of organic chemical compounds, thereby incorporating carbohydrate units into preexisting molecules and, for example, steroids. Employing the tools and methods disclosed, theoretically large numbers of novel steroidal molecules comprising carbohydrate units may be generated. As such, the subject invention provides for the generation and identification of novel molecular species which may act as agonists or antagonists of various biological, chemical or other activities.

The compounds provided by the present invention comprise the following general formulae:

$(X)_m-Z$ wherein:

X is a carbohydrate unit or modified carbohydrate unit;

Z is an activated functional group attached to a X at the anomeric position which carbon;

m is a positive integer;

with the proviso that at least one X does not have an oxygen at its anomeric position.

In a more specific embodiment, the activated carbon glycoside/heteroatom glycoside [$(X)_m-Z$] provided by the present invention is further defined as a compound comprising the following formula:

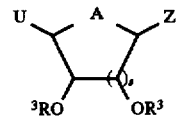

and pharmaceutically acceptable salts thereof, wherein:

Z is $-CH_2WCH_2T$, $-C\equiv CCH_2T$, $=C=CHCH_2T$, $-ArCH_2T$, $-(CH_2)_nV$;

W is $C=O$, $C=CR^1{}_2$, $CR^1CR^1{}_3$, $CR^1-CR^1{}_2OR^1$, $COR^1-CR^1{}_2OR^1$, $CR^1{}_2$, $CR^2-CR^2{}_2OR^3$, $CR^2-CR^2R^1{}_2$;

T is $O^-M^1$, $M^2$, $SR^1$, $S(O)R^1$, $SO_2R^1$, $P(O)OR^1{}_2$, COD, O—C(NH)CCl$_3$, $NR^1{}_2$;

V is $O^-M^1$, $SR^1$, $S(O)R^1$, $SO_2R^1$, $P(O)OR^1{}_2$, COD, $NR^1{}_2$;

n is a positive integer;

$M^1$ is $Na^+$, $K^+$, $Mg^{++}$, or $Ca^{++}$ ions;

$M^2$ is $Li^+$, $Mg^{++}$, $Ca^{++}$, $Cu^{++}$, $Cu^+$, ions;

$R^1$ is H, $CH_3$, lower alkyl;

$R^2$ is $OR^1$, $NR^1{}_2$, $SR^1$;

$R^3$ is $R^1$, protecting group, $SO_3M^1$, O-carbohydrate (linear or branched);

s is 1, 2, 3;

Protecting Groups include lower methyl-, benzyl-, MOM, MEM, MPM, tBDMS;

U is $CH_2OR^1$, $CH_2O$-protecting group, $CH_2OSO_3M^1$, $CH_2SO_3M^1$, $CH_2OR^3$, COD;

A is O, S, $NR^1{}_2CR^1{}_2$, $NR^1$;

D is $OR^1$, $NR^1{}_2$, $O^-M^1$;

Lower Alkyl is $C_1$ to $C_{10}$, branched or unbranched.
or:

Z is $CH_2$—W—$CH_2E$, —C≡$CCH_2E$, =C=$CHCH_2E$, —$ArCH_2E$, —$(CH_2)_nG$

W is C=O, C=$CR^1_2$, $CR^1CR^1_3$, $CR^1$—$CR^1_2OR^1$, $COR^1$—$CR^1_2OR^1$, $CR^1_2$, $CR^2$—$CR^2_2OR^3$, $CR^2$—$CR^2R^1_2$;

E is Cl, Br, I, OMs, OTf, OTs, OAc, O—$C(NH)CCl_3$;

G is Cl, Br, I, OMs, OTf, OTs, OAc, COD;

n is a positive integer;

$M^1$ is $Na^+$, $K^+$, $Mg^{++}$, or $Ca^{++}$ ions;

$R^1$ is H, lower alkyl;

$R^2$ is $OR^1$, $NR^1_2$, $SR^1$;

$R^3$ is $R^1$, protecting group, $SO_3M^1$, O-carbohydrate (linear or branched);

s is 1, 2, 3;

Protecting Groups include lower methyl-, benzyl-, benzoyl-, acetyl-, MOM, MEM, MPM, tBDMS, TMS;

U is $CH_2OR^1$, $CH_2$O-protecting group, $CH_2OSO_3M^1$, $CH_2SO_3M^1$, $CH_2OR^3$, COD;

A is O, S, $NR^1_2CR^1_2$, $NR^1$;

D is $OR^1$, $NR^1_2$, $O^{-M1}$;

Lower Alkyl is $C_1$ to $C_{10}$, branched or unbranched.

The present invention also provides methods for preparing modified steroids comprising a plurality of compounds wherein each compound is composed of one or a plurality of at least one monomer which is a modified carbohydrate. More specifically, the methods provide reacting $(X)_m$-Z, in a Z-primed reaction with a steroidal compound.

The compounds generated by the methods of the present invention may comprise an army of molecules with a diverse steroidal core structure, a diverse carbohydrate moiety or both. The carbohydrate moieties employed for the generation of such compounds include monomers, dimers, trimers, oligomers, branched or unbranched, linked to a suitable functional group of a chemical moiety comprising such functional group. Suitable functional groups include, but are not limited to, hydroxyl, carboxyl, thiol, amido, and amino groups.

In the case in which a moiety has more than one such suitable functional group, one or more such functional groups may be protected by suitable protecting groups during the coupling reaction. Such protecting groups include, but are not limited to, benzyl, or alkyl groups. After the coupling reaction, the protecting groups may selectively be removed.

The plurality of different steroidal members may be synthesized either in liquid phase or, alternately, linked to a solid synthesis support or in a mixture of both. After synthesis, the steroidal members may be cleaved from the synthesis support.

Still another aspect of the invention is to provide an array of novel steroidal chemical compounds comprising at least one carbohydrate unit, including a carbon glycoside/heteroatom glycoside, linked to a suitable derivatized functional group. The subject invention provides novel steroidal chemical compounds comprising the formula:

$(X)_m$-Z' wherein:

X is a carbohydrate unit or modified carbohydrate unit;

Z' is the reaction product of "Z" and asteroid, where Z is an activated functional group attached to a X at the anomeric position which is carbon;

m is a positive integer;

with the proviso that at least one X does not have an oxygen at its anomeric position.

The carbohydrate of the compound may be a monosaccharide, disaccharide, oligosaccharide or polysaccharide, either branched or unbranched. The carbohydrate units may comprise five membered ring structures, six membered ring structures, or both. The hydrogen of any hydroxy-group may be replaced by any compatible moiety. The molecular weight of the carbohydrate moiety ($X_m$) may less than or equal to the molecular weight of a monosaccharide (about 180), or several hundred thousand, as for example cellulose or other very complex sugars may have.

The anomeric C-atom of at least one carbohydrate unit does not comprise an oxygen. Rather, the oxygen is replaced by a sulfur-, nitrogen-, phosphorous-, silicon- or, most preferred, by a carbon-atom, to form a carbon glycosidic bond with the activated functional group "Z". This carbon glycosidic bond, in contrast to O-glycosidic bonds, tends to be hydrolytically and enzymatically stable.

The preferred steroidal glycoside compounds of the invention have the following structural formula 1:

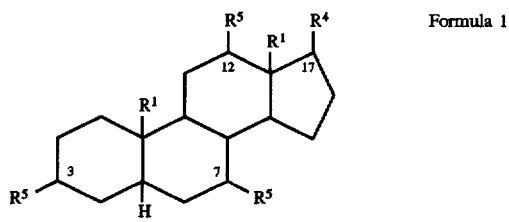

Formula 1

Wherein:

$R^1$ is H, $CH_3$, and lower alkyl.

$R^4$ is the steroidal 17-substituent preferably being in the 17-beta position of the steroid ring. $R^4$ can be C1–C8 alkyl including linear and branched alkyl and can be methyl, ethyl, propyl, isopropyl, isobutyl, isopentyl, and the like. Preferred is where the alkyl chain is 2,6-dimethylexyl, being the well-known 17-beta cholesterol side chain. $R^4$ further can be C2–C10 alkene, including linear or branched alkenes including, vinyl, propenyl, isopropenyl, n-butenyl, isobutenyl, isopentenyl, allyl and the like. 2,6-dimethyl-3-ethyl-hex-4-enyl, being the 17-stigmasterol side chain.

$R^4$ can further be

—$CH(CH_3)$—$(CH_2)_nCOD$

—$CH(CH_3)$—$(CH_2)_nCOR^5$

Where D is $OR^1$, $NR^1_2$, O—$M^1$;

The structure of formula 1 above may be in different isomeric forms and such are encompassed by this disclosure. In particular the carbon glycoside moiety may be in either the alpha or beta configuration and the linkage by which any sugar is attached to the steroid position may be either axial or equatorial. However, here and throughout the different stereo configurations are not shown but are understood to be encompassed by this disclosure.

$R^5$ is

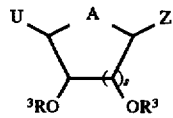

Z is a suitable linker unit, wherein the preferred linker units are —$CH_2WCH_2J$, —C≡$CCH_2J$, —C—$CHCH_2J$, —$ArCH_2J$, —$(CH_2)_nJ$ and;

W is C=O, C=CR$^1_2$, CR$^1$CR$^1_3$, CR$^1$—CR$^1_2$OR$^1$, COR$^1$—CR$^1_2$OR$^1$, CR$^1_2$, CR$^2$—CR$^2_2$OR$^3$, CR$^2$—CR$^2$R$^1_2$;

and where J attaches to the steroid ring and J is preferably oxygen, sulfur, or nitrogen;

n is a positive integer;

M$^1$ is Na$^+$, K$^+$, Mg$^{++}$, or Ca$^{++}$ions;

R$^1$ is H, CH$_3$, lower alkyl;

R$^2$ is OR$^1$, NR$^1_2$, SR$^1$;

R$^3$ is R$^1$, SO$_3$M$^1$, O-carbohydrate (linear or branched);

s is 1, 2, 3;

U is CH$_2$OR$^1$, CH$_2$O-protecting group, CH$_2$OSO$_3$M$^1$, CH$_2$SO$_3$M$^1$, CH$_2$OR$^3$, COD;

A is O, S, NR$^1_2$CR$^1_2$, NR$^1$;

D is OR$^1$, NR$^1_2$, O—M$^1$;

Lower Alkyl is C$_1$ to C$_{10}$, branched or unbranched.

With the proviso that at least one R$^5$ must be the carbon-glycoside/heteroatom-glycoside, then R$^5$ can also be R$^1$, oxo, —OSO$_3$M$^1$, —SO$_3$M$^1$, or O-carbohydrate (linear or branched).

DETAILED DESCRIPTION OF PREFERRED EMBODIMENTS

Unless defined otherwise all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein.

All publications, either scientific or patents, mentioned herein are incorporated by reference in this patent application in their entirety.

GLOSSARY

Terms are in general as typically used in the art. The following terms are intended to have the following general meanings as they are used herein:

Carbohydrate: As used herein "carbohydrate" is a chemical moiety comprising the general composition (C)$_n$(H$_2$O), including, but not limited to glucose, galactose, fucose, fructose, saccharose, mannose, arabinose, xylose, sorbose, lactose, and derivates, homo-/hetero-oligomers, homo-/hetero-polymers thereof, including but not limited to compounds which have other elemental compositions, such as aldonic acids, uronic acids, desoxysugars, or which contain additional elements or moieties, such as amino sugars, mucopolysaccharides wherein n is typically 4, 5, 6, or 7 and wherein the oxygen atom in the carbohydrate can be replaced by a heteroatom such as nitrogen, sulfur, carbon etc. A carbohydrate as used herein is understood to include chemical structures wherein the "H" of any hydroxy group is replaced by any chemically compatible moiety "R", which can be any monomer, oligomer or polymer in the meaning as used herein.

Carbohydrate Unit: As used herein, a "carbohydrate unit" is a monomer comprising a monosaccharide.

Carbon Glycoside: As used herein, a "carbon glycoside" is a carbohydrate derivative wherein the anomeric position does not have an oxygen but an atom other than oxygen, including carbon, nitrogen, sulfur, phosphorous and silicon (see, heteroatom glycoside).

Chemical Abbreviations: The following chemical abbreviations, as set forth below are used herein:

| Chemical Abbreviations. | |
|---|---|
| Ac | acetyl |
| 9-BBN | 9-borabicyclo[3.3.1]nonane |
| Bn | benzyl |
| Bz | benzoyl |
| CBn | p-chlorobenzyl |
| DHP | dihydropyran |
| DME | dimethoxyethane |
| DMF | N,N-dimethylformamide |
| Et | ethyl |
| Me | methyl |
| Ms | methanesulfonyl |
| sLe$^x$ | Sialyl Lewis$^x$ |
| TBAF | tetrabutylammonium fluoride |
| TBS or TBDMS | t-butyldimethylsilyl |
| Tf | trifluoromethanesulfonyl |
| THF | tetrahydrofuran |
| TMS | trimethylsilyl |
| TsOH | p-toluenesulfonic acid |
| TTN | thallium trinitrate |
| Ts | tosyl |

Functional Group: As used herein, a "functional group" comprises an atom or a group of atoms and their associated chemical bonds, acting as a unit that has about the same type of chemical reactivity whenever it occurs in different compounds.

Heteroatom Glycoside: As used herein, a "heteroatom glycoside" is a carbohydrate wherein the oxygen at the anomeric position is replaced by an atom other than oxygen, including carbon, nitrogen, sulfur, phosphorous and silicon.

Linker: A linker is that which joins or connects separate parts. A "linker" is a moiety, molecule, or group of molecules attached to a synthesis support or substrate and spacing a synthesized polymer or oligomer from the synthesis support or substrate. A "linker" can also be a moiety, molecule, or group of molecules attached to a substrate and spacing a synthesis support from the substrate.

A linker may be bi-functional, wherein said linker has a functional group at one end capable of attaching to a monomer, oligomer, synthesis support or substrate, a series of spacer residues, and a functional group at the end capable of attaching to a monomer, oligomer, synthesis support or substrate. The functional groups may be identical or distinct.

Monomer: As used herein, a "monomer" is any atom or molecule capable of forming at least one chemical bond. Thus, a "monomer" is any member of the set of atoms or molecules of any chemical nature, including inorganic and organic molecules that can be joined together as single units in a multiple of sequential or concerted chemical or enzymatic reaction steps to form an oligomer or polymer. Monomers may have one or a plurality of functional groups, which functional groups may be, but need not be, identical.

The set of monomers useful in the present invention includes, but is not restricted to, alkyl and aryl amines, alkyl and aryl mercaptans, alkyl and aryl ketones, alkyl and aryl carboxylic acids, alkyl and aryl esters, alkyl and aryl ethers, alkyl and aryl sulfoxides, alkyl and aryl sulfones, alkyl and aryl sulfonamides, phenols, alkyl alcohols, alkyl and aryl alkenes, alkyl and aryl lactams, alkyl and aryl lactones, alkyl and aryl di- and polyenes, alkyl and aryl alkynes, alkyl and aryl unsaturated ketones, aldehydes, 1,6-anhydrocarbohydrates, sulfoxides, sulfones, heteroatomic compounds containing one or more of the atoms of: nitrogen, sulfur, phosphorous, oxygen, and other polyfunctional molecules containing one or more of the above functional groups, L-amino acids, D-amino acids, deoxyribonucleosides, deoxyribonucleotides, ribonucleosides, ribonucleotides, sugars, benzodiazepines, β-lactams, hydantoins, quinones, hydroquinones, terpenes, and the like.

Monosaccharide: As used herein, a "monosaccharide" is any carbohydrate monomer or derivative thereof.

Named Reactions: As used herein, "Named Reactions" are chemical reactions which are chemical standard reactions known by the skilled artisan, including but not limited to the Alper Reaction, Barbier Reaction, Claisen-Ireland Reaction, Cope Rearrangement, Delepine Amine synthesis, Gewald Heterocycle Synthesis, Hiyama-Heathcock Stereoselective Allylation, Stork Radical Cyclization, Trost Cyclopentanation, Weidenhagen Imidazole Synthesis. See, in general, Hassner and Stumer, 1994. See, among other places, "Organic Syntheses Based on Named Reactions and Unnamed Reactions", Tetrahedron Organic Chemistry Series, edts. Baldwin and Magnus, Pergamon, Great Britain.

Protecting Groups: The moiety of the present invention may have groups protecting one or several inherent functional groups. Suitable "protecting groups" will depend on the functionality and particular chemistry used to construct the compounds. Examples of suitable functional protecting groups will be readily apparent to skilled artisans, and are described, for example, in Greene and Wutz, Protecting Groups in Organic Synthesis, 2d ed., John Wiley & Sons, N.Y. (1991), which is incorporated herein by reference.

Synthetic: A compound is "synthetic" when produced by chemical or enzymatic synthesis.

Transformation Event or Reaction: As used herein, a "transformation event" or "reaction" is any event that results in a change of chemical structure of a monomer, an oligomer or polymer. A "transformation event" or "reaction" may be mediated by physical, chemical, enzymatic, biological or other means, or a combination of means, including but not limited to, photo, chemical, enzymatic or biologically mediated isomerization or cleavage, photo, chemical enzymatic or biologically mediated side group or functional group addition, removal or modification, changes in temperature; changes in pressure, and the like. Thus, "transformation event" or "reaction" includes, but is not limited to, events that result in an increase in molecular weight of a monomer, an oligomer or polymer, such as, for example, addition of one or a plurality of monomers, addition of solvent or gas, or coordination of metal or other inorganic substrates such as, for example, zeolites. A "transformation event" or "reaction" may also result in a decrease in molecular weight of an oligomer or polymer, such as, for example, de-hydrogenation of an alcohol to form an alkene or enzymatic hydrolysis of an ester or amide. "Transformation events" or "reactions" also include events that result in no net change in molecular weight of a monomer, an oligomer or polymer, such as, for example, stereochemistry changes at one or a plurality of a chiral centers, Claissen rearrangement, Ireland rearrangement, or Cope rearrangement and other events as will become apparent to those skilled in the art upon review of this disclosure.

SYNTHETIC STRATEGY

Throughout this discussion, a standard numbering scheme for the steroidal nucleus will be referred to as described in the Merck Index for cholic acid. Merek 11 2206© 1989

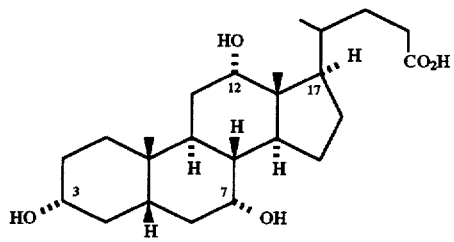

A large number of steroidal compounds may be employed as starting materials in the following synthetic strategy to yield steroidal C-glycosides. The preferred steroidal starting material will have a hydroxyl, or other reactive group, associated with the steroidal nucleus. More preferred are steroidal compounds that have a hydroxyl or other reactive group at the 3-, 7-, 12-positions of the steroidal nucleus and steroidal compounds that contain a hydroxyl group at the 3-position.

Synthesis of certain of the steroidal C-glycoside compounds of the invention requires manipulation about the hydroxyl positions of the steroidal nucleus. Some of these manipulations involve a double inversion methodology about this center.

The compound can be inverted from the β- to the α-form i.e. the $C_3$-β-OH to the $C_3$-α-OH using the Mitsunobu method (Mitsunobu, O. Synthesis (1981), 1) followed by use of the C-glycosidation procedures described herein.

Other Synthetic Aspects

The synthesis of other compounds containing alternate carbohydrates attached to the carbon linking arms for the glycoside conjugates are accomplished by usual glycosidation methods. Alternately, any carbohydrate unit being charged or uncharged and/or deoxygenated species can be formed using the carbon- procedure given in this disclosure, but this disclosure does not exclude the analogs prepared from branched, linear or other forms of di-, tri- and poly saccharides or oligosaccharides or combinations. The derivatized carbon-glycoside can be further utilized as a linking group between a pyran ring and the spacer attached to the steroidal C-glycoside nucleus by a selective protection methodology involving use of a 2'3'-benzylidene derivative in which selective rearrangement and/or functionalization and/or glycosidation can be accomplished prior to deprotection. Thus, the various derivatives are converted to potentially more useful compounds.

Multivalent Forms of Steroidal C-Glycosides

The affinity of the compounds of the invention for a receptor can be enhanced by providing multiple copies of the steroidal C-glycoside in close proximity, preferably using a scaffolding provided by a carrier moiety. It has been shown that provision of such multiple valence with optimal spacing between the moieties dramatically improves binding to a receptor. (See, for example, Lee, Y. C. et al., Biochem 23:4255 (1984)).

The multivalency and spacing can be controlled by selection of a suitable carrier moiety. Such moieties include but are not limited to molecular supports which contain a multiplicity of functional groups that can be reacted with functional groups associated with the compounds of the invention. A particularly preferred approach involves coupling of the compounds of the invention to amino groups of the carrier through reductive amination. Reductive amination is a particularly convenient way to couple aldehyde moieties to free amino groups by first forming the Schiff base and then treating the conjugate with a reducing agent, such as a hydride reducing agent. Typically, the amino group-bearing carrier is mixed with the carbohydrate moiety at about pH 9 and allowed to form the Schiff base; the solvents are typically evaporated and a reducing agent is added at high pH to complete the reaction.

Particularly convenient carrier moieties to obtain multivalent forms of the invention compounds include (amines (e.g. $N(CH_2CH_2NH_2)_3$), proteins and peptides, particularly those containing lysyl residues which have ω-amino groups available for binding. It is also useful to include in the peptide or protein at least one tyrosine residue, as this offers a convenient site for labeling, for example with radioactive iodine. A particularly convenient carrier to obtain a trivalent couple is the peptide Lys-Tyr-Lys. Complete reaction of the compounds of the invention with the free amino groups on this peptide result in a trivalent moiety. Thus, for example, compounds of the invention of the general formula (2) may be used to make multivalent constructs:

USE AND ADMINISTRATION

The steroidal C-glycoside derivatives of the invention can be administered to a subject in need thereof to treat the subject by either prophylactically preventing inflammation or relieving it after it has begun. The compounds are preferably administered with a pharmaceutically acceptable carrier, the nature of the carrier differing with the mode of administration, for example, oral administration, usually using a solid carrier and I.V. administration of a liquid salt solution carrier. The formulation of choice can be accomplished using a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of the subject steroidal C-glycoside molecules directly in transdermal formulations with perme-

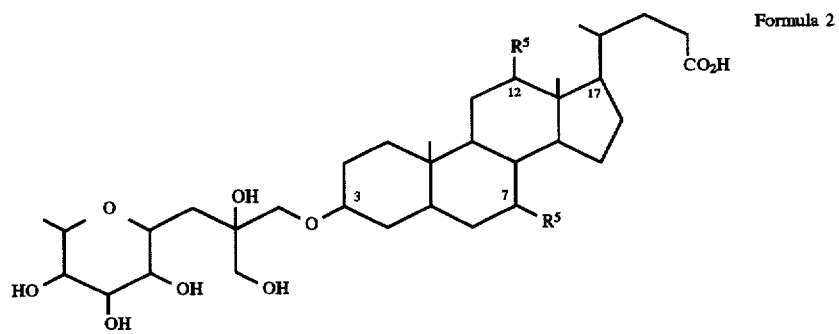

Formula 2

Of course, a variety of carriers can be used, including proteins such as BSA or HSA, a multiplicity of peptides including, for example, pentapeptides, decapeptides, pentadecapeptides, and the like. Preferably, the peptides or proteins contain the desired number of amino acid residues having free amino groups in their side chains; however, other functional groups, such as sulfhydryl groups or hydroxyl groups can also be used to obtain stable linkages. For example, the steroid or carbohydrate compounds of the invention may be oxidized to contain carboxyl groups or utilize the carboxyl groups which can then be derivatized with either free amino groups to form amides or with hydroxyl groups to form esters. In addition, a suitably functionalized biotin tether may be attached with subsequent complexation with avidin for mulitvalent forms.

The structure of formula (1 and 2) above may be in different isomeric forms and such are encompassed by this disclosure. In particular, the carbon glycoside moiety may be in either the alpha or beta configuration and the linkage by which any sugar is attached may be either axial or equatorial. For instance, acetates and benzoates may serve as protecting groups for the hydroxyl groups in sugars and display neighboring group participation in glycosidation reactions. Thus, by judicious choice of protecting groups prior to the glycosidation, i.e., benzyl ethers, acetates or benzoates, one can preferentially select for either the alpha- or beta- carbon linked glycosides (H. Paulsen, Angew Chem. Int. Ed. Engl., 21:155 (1982); R. R. Schmidt, "Synthesis of Carbon linked glycosides in Comprehensive Organic Synthesis", Ed. B. M. Trost, 6:33–64). Thus, here and throughout the different stereo configurations are not shown but are understood to be encompassed by this disclosure and the appended claims.

ation enhancers such as DMSO. Other topical formulations can be administered to treat dermal inflammation.

An animal model that is particularly useful for testing the anti-inflammatory activity of the invention compounds is the arachidonic acid (AA), murine skin inflammation model, described by Harris, R. R. et al. (Skin Pharmacol 3:29–40 (1990). Arachidonic acid is known to induce an inflammatory response and the compounds were tested for their capacity to inhibit the response.

Briefly, the compounds at an appropriate concentration are dissolved in a suitable solvent, and applied to a rodent ear immediately following application of arachidonic acid (AA). A control of AA alone is run. About 90 minutes later, a 6 mm disk of each ear is removed and weighed. The percent inhibition of swelling caused by AA alone is calculated for the steroidal C-glycoside derivatives of the invention and compared to other steroids.

A sufficient amount of the desired steroidal C-glycoside is preferrably administered that binds to a substantial portion of one or more of the selectins so that inflammation can either be prevented or ameliorated. Thus, "treating" as used herein shall mean preventing or ameliorating inflammation and/or symptoms associated with inflammation. Typically, the compositions of the instant invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based on patient responsiveness. Other effective dosages can be readily determined by one of ordinary skill in the art through routine trials establishing dose response curves.

In determining the dose of compounds to be administered, it must be kept in mind that one may not wish to completely block all of the receptors. In orderfor a normal healing process to proceed, at least some of the white blood cells or neutrophils must be brought into the tissue in the areas where the wound, infection or disease state is occurring. The amount of the compounds administered as blocking agents must be adjusted carefully based on the particular needs of the patient while taking into consideration a variety of factors such as the type of disease that is being treated.

It is believed that the compounds or blocking agents of the present invention can be used to treat a wide range of diseases, including diseases such as rheumatoid arthritis and multiple sclerosis. The compositions of the invention should be applicable to treat any disease state wherein the immune system turns against the body causing the white cells to accumulate in the tissues to the extent that the accumulated white cells cause tissue damage, swelling, inflammation and/or pain. The inflammation of rheumatoid arthritis, for example, is created when large numbers of white blood cells quickly enter the joints in the area of disease and attack the surrounding tissues.

Formulations of the present invention might also be administered to prevent the undesirable aftereffects of tissue damage resulting from heart attacks. When a heart attack occurs and the patient has been revived, such as by the application of anticoagulants or thrombolytic (e.g., tPA), the endothelial lining where a clot formed has often suffered damage. When the antithrombotic has removed the clot, the damaged tissue beneath the clot and other damaged tissue in the endothelial lining which has been deprived of oxygen, become activated. The activated endothelial cells then synthesize the ELAM-1 receptors within hours of the cells being damaged. Large numbers of white blood cells are quickly captured and brought into the tissue surrounding the area of activated endothelial cells, resulting in inflammation, swelling and necrosis which thereby decreases the likelihood of survival of the patient.

In addition to treating patients suffering from the trauma resulting from heart attack, patients suffering from actual physical trauma could be treated with formulations of the invention in order to relieve the amount of inflammation and swelling which normally result after an area of the body is subjected to severe trauma. Other disease states which might be treatable using formulations of the invention include various types of arthritis and adult respiratory distress syndrome. After reading the present disclosure, those skilled in the art will recognize other disease states and/or symptoms which might be treated and/or mitigated by the administration of formulations of the present invention.

Other modes of administration will also find use with the subject invention. For instance, the steroidal C-glycoside molecules of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

The compounds of the instant invention may also be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles. The compounds of structural formula 1 can be mixed with compatible, pharmaceutically acceptable excipients.

Suitable vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the steroidal C-glycoside molecules adequate to achieve the desired state in the subject being treated.

The various compounds of the present invention can be used by themselves or in combination with pharmaceutically acceptable excipient materials as described above. However, the compounds of the invention can be made as conjugates wherein the compounds of the invention are linked in some manner to a label. By forming such conjugates, the steroidal C-glycoside compounds of the invention act as biochemical delivery systems for the label so that a site of inflammation can be detected.

The steroidal C-glycoside molecules of the invention could also be used as laboratory probes to test for the presence of a selecting receptor in a sample. Such probes are preferably labeled such as with a radioactive, fluorescent or enzyme activated label.

It should also be pointed out that various "linker" groups can be attached to the steroidal C-glycoside compounds of the invention, and the linker groups can be used to attach various additional compounds such as pharmaceutically acceptable drugs. By using the linker various conjugates are formed i.e. Steroidal C-glycoside-linker-drug conjugates are formed which provide effective drug delivery systems for the drug which is linked to the steroidal C-glycoside compound of the invention. It is especially preferred to attach a drug with anti-inflammatory characteristics in that the steroidal C-glycoside binds to one or more selectins which are associated with inflammation. Accordingly, non-steroidal anti-inflammatory drugs (NSAIDs) such as naproxen or ibuprofen which act as anti-inflammatory agents could be administered bound to the steroidal C-glycoside and could be administered systemically in smaller amounts than usual while obtaining an equivalent effect or even greater anti-inflammatory effect at the site of inflammation. The drug could be attached by an enzymatically cleavable linker which linker is cleaved by an enzyme such as an esterase. Any other drugs which might be attached include, but are not limited to, antibiotics, vasodilators and analgesics. Such a drug delivery system would reduce any systemic effect normally caused by the drug in that the drugs could be administered in amounts of one-half to one-tenth the normal dose and still obtain the same anti-inflammatory result at the site of inflammation, without adverse side effects. Other drug delivery systems may be polymeric backbones which may be, but not limited to, simple polymers, polymeric carbohydrates, cyclodextrins, heparin or its derivatives, peptides, polymeric beads. etc.

Before the present compounds and compositions, and processes for isolating and using such are described, it is to be understood that this invention is not limited to the particular compositions, methods or processes described as such may, of course, vary as would be known by the skilled practitioner of this art. It is also to be understood that the terminology used herein is for the purpose of describing particular embodiments only, and is not intended to be limiting since the scope of the present invention will be limited only by the appended claims.

Synthesis of Carbon Glycosides

A vast array of methods for carbon-carbon bond formation at the anomeric carbon are known in the art, which also can be applied to the formation of other heteroatom glycosides, such as carbon-phosphorous, carbon-sulfur, carbon-nitrogen, or carbon-silicon bonds at the anomeric position which are understood to be within the invention. The most common method for carbon-carbon bond formation at the anomeric carbon involves nucleophilic attack on this electrophilic center. A wide variety of electrophilic sugars have been employed, such as glycosyl halides, imidates, glycals, lactones, thioglycosides, as well as oxygen-protected glycosides such as p-nitrobenzoates. The carbon nucleophiles that have been used include silyl enol ethers, alkenes, allylsilanes, allylstannanes, homoenolates, and organometallics such as Grignard reagents, organolithiums, cuprates, and aluminates. Further, procedures to synthesize carbon-glycosides based on metals (palladium, manganese, rhodium, and cobalt) have been developed. Concerted reactions such as [4+2] cycloadditions and sigmatropic rearrangements have also been employed to generate carbon glycosides. Also the field of free radical chemistry has been extended to this area; the special merits of free radical methods are mild reaction conditions and tolerance of a wide range of functional groups. The subject of carbon-glycoside synthesis has been reviewed by Hanessian and Pernet, 1976, Adv. Chem. Biochem. 33:111; Suhadoluid, 1970, Nucleoside Antibiotics Wiley-Interscience: New York; and Daves and Cheng, 1976, Prog. Med. Chem. 13:303; Inch, 1984, Tetrahedron 40:3161; Hacksell and Daves, 1985, Prog. Med. Chem. 22:1;and Buchanan, 1983, Prog. Chem. Org Natl. Prod. 44:243.

The following scheme shows the general chemical reaction underlying the generation of activated carbon glycosides useful for the generation of novel compounds provided by the present invention:

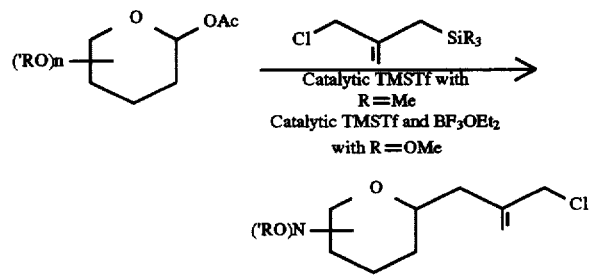

The typical procedure to make carbon—carbon bonds at the anomeric carbon involves nucleophilic attack on the electrophilic center. A wide variety of electrophilic sugars have been employed, such as reducing sugars (or lactols), alkyl glycosides, anomeric esters, anomeric trichloroacetimidates, and glycosyl halides. The carbon nucleophiles that have been used include silyl enol ethers, olefins, allyl-, propargylsilanes, cyanides, homoenolates, and organometallics such as Grignard reagents, organolithiums, cuprates, and aluminates. These reactions can be used to modify the anomeric position. Protecting groups typically used when modifying the anomeric position of carbohydrates should be apparent to the skilled artisan. In addition, a plurality of functional groups may be employed. The C-atom of the carbohydrate used for the formation of the carbon glycosidic bond can be modified by differential protection of functional groups, as will be apparent to those skilled in the art. Techniques and methods for the protection of functional groups can be found, among other places, in Greene and Wutz, supra. An array of different reaction types have been employed for the generation of carbon glycosides (Postema, 1992, Tetrahedron 48:8545; Postema, C-Glycoside Synthesis, 1995, CRC Press, Ann Arbor, Mich.): For example, concerted reactions, such as the sigmatropic rearrangement or cycloadditions as the Dieis-Alder Reaction can be used for the formation of carbon glycosides. Also, the Wittig Reaction has extensively been applied to carbon glycoside synthesis, which can be pursued by reaction of hemiacetals followed by ring closure, reaction of sugar lactones, or reaction of anomeric phosphoranes. Other approaches for the synthesis of carbon glycosides encompass, among others, palladium mediated reactions, free radical reactions, and reactions relying on the electrophilic activity of the anomeric center of sugar molecules. These methods are readily known by the skilled artisan.

Reagents efficient for the preparation of carbon glycosides include allyltrimethylsilane (Herscovici and Antonakis, 1992, Nat. Prod. Chem. 10:337; Postema, 1992, Tetrahedron 48:8545; Daves, 1990, Acc. Chem. Res. 23:201; Hacksell, 1985, Progress in Medicinal Chemistry 22:1; Hanessian and Pernet, 1976, Adv. Chem. Biochem. 33:111; Carbohydrate Chemistry, Specialist Periodical Reports, Royal Chemical Society, 1968–1990, p. 1–24; preparation of allyl silanes: Anderson and Fuchs, 1987, Synthetic Commun. 17:621) and an array of carbon nucleophiles available from commercial sources. Additional examples include, trimethylsilyl enol ethers, allyltrimethylsilane, E- and Z-crotyltrialkylsilanes, organoaluminum reagents, trialkylstannanes, propargylic trialkylstannanes, [1-(acetoxy)-2-propenyl]trimethylsilane, [1-(acetoxy)-2-methyl-2-propenyl]-trimethylsilane, and ethyl-2-propenyltrimethyl-silane-1-carbonate. All are efficient carbon nucleophiles in the field of carbon glycosidation reactions (Panek and Sparks, 1989, J. Org. Chem. 54:2034, and references therein). The use of [1-(acetoxy)-2-methyl-2-propenyl]-trimethylsilane reagent provides access to terminally oxygen substituted propenyl groups.

Although carbon glycosides can be produced in a few synthetic transformations, they do not necessarily form suitable carbon glycosides which could easily be used as alkylating agents for the preparation of novel carbohydrate mimics. In one aspect, the present invention provides novel carbohydrate mimetics. Using the present invention, libraries of glycomimetics of complex carbohydrates such as, but not limited, to Sialyl Lewis$^x$ (sLe$^x$) tetrasaccharide can be prepared (Raoet el., 1994, The Journal of Biological Chemistry 269:19663; Allanson et al., 1994, Tetrahedron Asymmetry 5:2061). One of the advantages of having an allylic halide as an alkylating agent is it would not be prone to E-2 elimination reactions (see, among other places, Lowry and Richardson, Mechanisms and Theory in Organic Chemistry, Second edition, 1981, Harper & Row, New York, p. 530). Among the distinct advantages of this type of novel carbon glycoside is in the plethora of new chemical entities created by virtue of the invention.

For example, several terminally substituted halogen carbon glycosides are efficiently obtained from reaction of 2-chloromethyl-3-trimethylsilyl-1-propene or 2-chloromethyl-3-trimethoxysilyl-1-propene with an activated carbohydrate when the reaction is catalyzed by Lewis acid. Thereby, the allylsilanes can undergo a stereochemically controlled axial addition to the pyranose oxonium ions produced by Lewis acid catalysis and anomeric acetates. Benzyl protected carbohydrates result in a stereo selective and efficient route to α-C-glycosides, incorporating an allylic chloride. The use of the per-O-acetylated carbohydrates offers added versatility by avoiding the hydrogenolysis step required for O-benzyl protected sugars. Nashed and Anderson, 1982, *J. Amer. Chem. Soc.* 104:7282; Panek and Sparks, 1989, *J. Org. Chem.* 54:2034. 2-chloromethyl-3-trimethylsilyl-1-propene and 2-chloromethyl-3-trimethoxysilyl-1-propene reagents react with benzyl protected carbohydrates with equal efficiency while per-O-acetylated carbohydrates show better results with the 2-chloromethyl-3-trimethylsilyl-1-propene reagent. Examples for the carbon glycoside synthesis as employed by the subject invention are provided by the instant disclosure, infra. Both the α- and the β-configurations are part of the invention.

EXAMPLES

The following examples are put forth so as to provide those of ordinary skill in the art with a complete disclosure and description of how to make the compounds and compositions of the invention and are not intended to limit the scope of what the inventors regard as their invention. Efforts have been made to ensure accuracy with respect to numbers that would be used (e.g., amounts, temperature, etc.) but some experimental errors and deviations should be accounted for. Unless indicated otherwise, parts are parts by weight, molecular weight is weight average molecular weight, temperature is in degrees centigrade and pressure is at or near atmospheric.

Certain materials and methods are described in the following representative patent applications: "Derivatives of Triterpenoid Acids and Uses Thereof." (U.S. Ser. No. 08/049,018 filed Apr. 16, 1993); "Lupane Triterpenoid Derivatives" (U.S. Ser. No. 08/105,095 filed Aug. 9, 1993); "Glycomimetic Combinatorial Libraries" (U.S. Ser. No. 08/446,185, filed May, 19, 1995). These and all other references cited herein are hereby incorporated by reference in their entirety.

The instant invention is shown and described herein in what are considered to be the most practical and preferred embodiments. It is recognized, however, that departures may be made therefrom which are within the scope of the invention, and that obvious modifications will occur to one skilled in the art upon reading this disclosure.

Materials

Reagents were purchased from commercial suppliers such as Pfanstiehl Laboratories, Aldrich Chemical Company or Lancaster Synthesis Ltd. and were used without further purification unless otherwise indicated. Tetrahydrofuran (THF) and dimethylformamide (DMF) were purchased from Aldrich in sure seal bottles and used as received. All solvents were purified by using standard methods readily known to those skilled in the art unless otherwise indicated.

General Protocol

The reactions set forth below were done generally under a positive pressure of nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (tlc) was performed on glass-backed silica gel 60 F 254 plates Analtech (0.25 mm) and eluted with the appropriate solvent ratios (v/v) and are denoted where appropriate. The reactions were assayed by tlc and terminated as judged by the consumption of starting material.

Visualization of the tlc plates was done with a p-anisaldehyde spray reagent or phosphomolybdic acid reagent (Aldrich Chemical 20% wt in ethanol) and activated with heat.

Work-ups were typically done by doubling the reaction volume with the reaction solvent or extraction solvent and then washing with the indicated aqueous solutions using 25% by volume of the extraction volume unless otherwise indicated.

Product solutions were dried over anhydrous $Na_2SO_4$ prior to filtration and evaporation of the solvents under reduced pressure on a rotary evaporator and noted as solvents removed in vacuo.

Flash column chromatography (Still et al., 1978, *A. J. Org. Chem.* 43:2923) was done using Baker grade flash silica gel (47-61 mm) and a silica gel: crude material ratio of about 20:1 to 50:1 unless otherwise stated. Sulfated compounds were purified on P2 gel columns and eluted with aqueous ammonium carbonate or ammonium acetate, or on Iatron beads available from Iatron Laboratories, Tokyo, Japan.

Hydrogenolysis can be done at the pressure indicated in the examples, or at ambient pressure.

$^1$H-NMR spectra were recorded on a Varian 300 instrument operating at 300 MHz and $^{13}$C-NMR spectra were recorded on a Varian 300 instrument operating at 75 MHz. NMR spectra were obtained as $CDCl_3$ solutions (reported in ppm), using chloroform as the reference standard (7.25 ppm and 77.00 ppm) or $DC_3OD$ (3.4 and 4.8 ppm and 49.3 ppm) or internal tetramethylsilane (0.00 ppm) when appropriate. When peak multiplicities are reported, the following abbreviations are used: s (singlet), d (doublet), t (triplet), m (multiplet), br (broadened), dd (doublet of doublets), or dt (doublet of triplets). Coupling constants, when given, are reported in Hertz.

Infrared spectra were recorded on a Perkin-Elmer FT-I R Spectrometer as neat oils, or as $CDCl_3$ solutions, and are reported in wave numbers ($cm^{-1}$).

The mass spectra were obtained using LSIMS. All melting points are uncorrected. Microanalyses were carried out by Galbraith Laboratories, Inc., Knoxville, Tenn.

General Experimental Procedures

The skilled artisan will appreciate and understand the following general experimentals as they are used in the art to prepare novel compounds from the invention. The mmole equiv refers to the reaction substrate to be functionalized by the reaction with the carbon glycoside reagent per position to be alkylated. Additional functional group transformations can be accomplished by the skilled artisan using standard reaction conditions. For example, the transformation of allylic halides into allylic amines can be via the allylic azide with reduction of the azide to the amine with triphenylphosphine in water. The amine is then available for amide bond formation.

General Alkylation conditions using a Sodium Hydride and an Aliphatic Alcohol

To a mechanically stirred solution of sodium hydride (3.00 mmole equiv. Note: the sodium hydride is washed three times with hexanes prior to use.) in THF (slurry) at ambient temperature is added an aliphatic alcohol (1.00 mmole equiv.) dropwise in a minimum of anhydrous tetrahydrofuran. Thetrabutylammonium iodide (0.10 mmole equiv.) is added and the reaction contents are stirred at room temperature (slight warming to above room temperature is sometimes needed for the initiation of the reaction) for 60 minutes in order to minimize the rate of gas evolution. The reaction contents are warmed for a period of 2 hours, carefully watching for the evolution of hydrogen. The reaction contents are stirred using a mechanical stirrer while being gently refluxed for a period of 1.5 hours. A benzyl protected carbon glycoside reagent (1.50 mmole equiv.) is slowly added dropwise in anhydrous tetrahydrofuran (total reaction concentration of 0.2 to 0.5M) over a period of 1–2 hours and stirred for 4 hours. An aliquot of the reaction contents is removed and quenched into 1.0M HCl and extracted with ethyl acetate; the tlc conditions used are 5% methanol in chloroform (v/v). The reaction is then diluted with toluene and terminated by the careful addition of 50% methanol in toluene at 0° C. to consume the residual sodium hydride, followed by acidification with 1.0M hydrochloric acid until the pH is ~2. The reaction contents are diluted with ethyl acetate. The heterogeneous layers are separated and the organic phase is washed twice with portions of 1.0M hydrochloric acid, saturated sodium thiosulfate and brine. The product can be purified by column chromatography using Baker grade flash silica gel (47–61 mm) and a suitable solvent system. For example, 10% ethyl acetate in hexanes may be used followed by 30% ethyl acetate in hexanes. The silica gel is eluted with methanol and checked by tlc for any product material. The solvents are removed in vacuo and the product dried under vacuum. The desired product is recovered.

Bis-hydroxylation of the Olefin via Oxidation with Osmium Tetroxide.

To a stirred solution of the olefin, (1.00 mmole equiv.) in 1% water in acetone (0.5M) at 0° C. is added osmium tetroxide pre-dissolved in acetone (0.01 mmole equiv.) and N-methylmorpholine-N-oxide (2.00 mmole equiv.) is carefully added as a solid. The reaction contents are stirred at 0° C. and the cooling bath (water/ice) is allowed to melt. The reaction is allowed to stir at ambient temperature for 18 hours or until the reaction is complete via analysis by tlc. The reaction can be assayed by TLC or an aliquot of the reaction acetate. The aliquot is checked by $^1$H-NMR in CDCl$_3$. The reaction is terminated by the careful addition of sodium bisulfite (a mixture of NaHSO$_3$ and Na$_2$S$_2$O$_5$), stirred for 1 hour at room temperature and then water is added. An extraction solvent such as chloroform is added and the heterogeneous layers are separated and the organic phase is washed with 1.0M hydrochloric acid, water and brine. The washed product is dried over anhydrous sodium sulfate and filtered. The product can be purified by column chromatography using Baker grade flash silica gel (47–61 mm) and a suitable solvent system for example, 10% ethyl acetate in hexanes and then with 30% ethyl acetate in hexanes. The silica gel is eluted with methanol and checked by tlc for any product material. The solvents are removed in vacuo and the product dried under vacuum and the desired product is recovered.

Oxidation of the Alkene to the Ketone via Catalytic Oxidation with Osmium Tetroxide and Sodium Periodate.

To a stirred solution of the olefin, (1.00 mmole equiv.) in 1% water in acetone (0.5M) at 0° C. is added osmium tetroxide pre-dissolved in acetone (0.01 mmole equiv.) and sodium periodate (2.00 mmole equiv.) is carefully added as a solid. The reaction contents are stirred at 0° C. and the cooling bath (water/ice) is allowed to melt and the reaction allowed to stir at ambient temperature for 18 hours or until the reaction is complete via analysis by tlc. The reaction can be assayed by TLC or an aliquot of the reaction contents is removed, quenched into aqueous sodium metasulfite and extracted with ethyl acetate. The aliquot is checked by $^1$H-NMR in CDCl$_3$. The reaction is terminated by the careful addition sodium bisulfite (a mixture of NaHSO$_3$ and Na$_2$S$_2$O$_5$), stirred for 1 hour at room temperature and then water. An extraction solvent such as chloroform is added and then washed with hydrochloric acid, water and brine. The washed product is dried over anhydrous sodium sulfate and filtered. The product can be purified by column chromatography using Baker grade flash silica gel (47–61 mm) and a suitable solvent system, for example, 10% ethyl acetate in hexanes and then with 30% ethyl acetate in hexanes. The silica gel is eluted with methanol and checked by tlc for any product material. The solvents are removed in vacuo and the product dried under vacuum. The desired product is recovered.

Catylitic Hydrogenation for the removal of Benzyl Protecting Groups.

For a compound containing benzyl protecting groups, a 1.00 mm equiv. is dissolved in an appropriate hydrogenation solvent suitable for the compound to be deprotected. For example, the solvent could be methanol with a catalytic amount of acetic acid or ethyl acetate and methanol. 5% or 10% palladium on carbon (1 g for every 50 grams of starting material with the catalyst wetted with 50–100 mL of toluene under argon) is evacuated and hydrogen gas is added and the process repeated three times. The reaction is shaken or stirred for several hours until the deprotection is complete. The reaction is terminated by filtering the contents through Celite to remove the catalyst and washing the catalyst with 30% methanol in chloroform. Concentration in vacuo affords the desired compound. The product can be purified by column chromatography using Baker grade fresh silica gel (47–61 mm) and a suitable solvent system, for example, 10% ethyl acetate in hexanes and then with 30% ethyl acetate in hexanes. The silica gel is eluted with methanol and checked by tlc for any product material. The solvents are removed in vacuo and the product dried under vacuum. The desired product is recovered.

Sulfation of Hydroxyl Functionalities.

To a solution of the alcohol(s) groups to be sulfated from the products of the invention (1.00 mmole equiv.) in anhydrous dimethylformamide (0.2M) at ambient temperature was added sulfur trioxide pyridine complex of the sulfur trioxide pyridine complex polymer bound [Graf, W. chem. Ind. 1987, 232.] (10 mmole equiv.). The reaction contents were stirred at ambient temperature for 8 hours. The reaction was quenched using sodium carbonate, the solvents were removed by lyophilization and the resulting material was subjected to sodium ion exchange resin for the exchange of residual ionic salts for sodium ions. Concentration in vacuo affords the sulfated materials.

To a solution of the alcohol(s) groups to be sulfated from the products of the invention (1.00 mmole equiv.) in anhydrous pyridine (0.5M) at 0° C. was added sulfur trioxide pyridine complex (10 mmole equiv.). The reaction contents were stirred at ambient temperature for 8 hours. The reaction was quenched using methanol and the solvents were removed by rotary evaporation with added pyridine (1–5%). Chromatography of the crude sulfated materials was performed on Iatro beads available from Iatron Incorporated in Tokyo, Japan. Elution solvents were typically 80/20/2/1 of dichloromethane/methanol/water/pyridine or suitable ratios of these to give a Rf on tlc of approximately 0.25 to 0.30. Ion exchange was done in water by passing the product through a sodium ion exchange resin (rinsed with water prior to use). Lyophilization gave the desired salt form of the product.

a small pad of silica gel. The solvent was removed in vacuo which afforded an oil that was chromatographed on Baker grade flash silica gel (47–61 mm) (ratio of 50 to 1) and eluted with 5 or 10% ethyl acetate in hexanes. Concentration in vacuo afforded 20.01 g of 2-Chloromethyl-3-(tri-O-benzyl-alpha-L-C-fucopyranoside)-1-propene (1) (85%)

Example 2

Preparation of 2-(tri-O-benzyl-alpha-L-C-methylfucopyranose)-3-[3-O-(Lithicholic acid)]-1-Propene (2).

The following compound was prepared as follows.

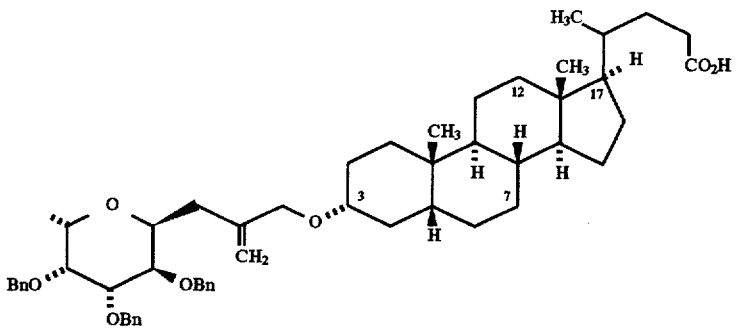

30

Concentration in vacuo affords the sulfated materials. Sulfated compounds were purified on P2 gel columns and eluted with aqueous ammonium carbonate or ammonium acetate, or on Iatro beads available from Iatron Laboratories, Tokyo, Japan.

Example 1

Preparation of Key Synthetic Intermediate

2-Chloromethyl-3-(tri-O-benzyl-alpha-L-C-fucopyranoside)-1-propene (1)

The following synthetic chemical intermediate compound that was used to prepare the final invention compounds was synthesized as now described.

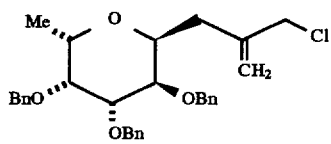

To a solution of tri-O-benzyl-L-fucopyranose (20.0 g, 46.03 mmole, 1.00 mmole eqiv.) in anhydrous acetonitrile (200 mL) at 0° C. was added 2-chloromethyl-3trimethylsily-1-propene (30.0 g, 184.34 mmole, 4.00 mmole eqiv.). Trimethylsilane trifluoromethane sulfonic acid (10.24 g, 46.03 mmol, 1.00 mmole eqlv.) was added dropwise in anhydrous acetonitrile (30 mL, overall reaction concentration 0.2M) and the reaction contents stirred at 0° C. for 30 minutes. After 30 minutes, the reaction was diluted with ethyl acetate (230 mL) and the reaction was terminated by pouring the contents slowly into aqueous saturated sodium bicarbonate. The heterogeneous layers were separated and the organic phase was washed twice with portions of water, 1.0M hydrochloric acid and brine. The crude product was dried over anhydrous sodium sulfate, filtered and plugged through To a solution of sodium hydride (382 mg, 15.9 mmole, 6.00 mmole equiv.) in anhydrous 25% dimethylformamide in tetrahydrofuran (17.5 mL) at ambient temperature was added Lithocholic acid (1.00 g, 2.65 mmol, 1.00 mmole equiv.) in a minimum amount of anhydrous 25% dimethylformamide in tetrahydrofuran. Sodium iodide (3.97 g, 26.5 mmole, 10.00 mmole equv.) and Tetra-n-butylammonium Iodide (97 mg, 0.265 mmole, 0.10 mmole equiv.) were added and the reaction contents were warmed to a gentle reflux (until the evolution of $H_2$ ceased) for 30 minutes. 2-Chloromethyl-3-(tri-O-benzyl-alpha-L-C-fucopyranoside)-1-propene (1) (4.04 g, 7.96 mmole, 3.00 mmole equiv.) was added dropwise in anhydrous 25% dimethylformamide in tetrahydrofuran (17.5 mL, total of 0.08M) and gently refluxed for 6 hours. After 6 hours at reflux, the reaction was terminated by the careful addition of 50% methanol in toluene (10 mL) at 0° C. and then 4M hydrochloric acid until the pH was 1–2 and then diluted with ethyl acetate. The heterogeneous layers were separated and the organic phase was washed with portions of 1.0M hydrochloric acid, sodium bicarbonate and brine. The crude product was dried over anhydrous sodium sulfate, filtered and plugged through a small pad of silica gel eluting with ethyl acetate. The solvent was removed in vacuo which afforded an oil that was chromatographed on Baker grade flash silica gel (47–61 mm) (ratio 50 to 1) and eluted with benzene, 10% ethyl acetate in hexane, 30% ethyl acetate in hexane, 50% ethyl acetate in hexane, 100% ethyl acetate and finally with 5% methanol in chloroform. Concentration in vacuo afforded 1.46 g of 2-(tri-O-benzyl-alpha-L-C-methylfucopyranose)-3-[3-O-(Lithocholic acid) ]-1-propene (2) (51–65%) as a white foam powder.

An alternate procedure to prepare 2-(tri-O-benzyl-alpha-L-C-methylfucopyranose)-3-[3-O-(Lithocholic acid)]-1-propene (2) is as follows. To a solution of sodium hydride (382 mg, 15.9 mmole, 6.00 mmole equiv.) in anhydrous benzene (17.5 mL) at ambient temperature is added Lithocholic acid (1.00 g, 2.65 mmol, 1.00 mmole equiv.) dropwise in a minimum amount of anhydrous tetrahydrofuran. Sodium iodide (3.97 g, 26.5 mmole, 10.00 mmole equv.) and Tetra-n-butylammonium Iodide (97 mg, 0.265 mmole, 0.10 mmole equiv.) are added and the reaction contents are warmed to a gentle reflux (until the evolution of $H_2$ ceased) for 30 minutes. 2-Chloromethyl-3-(tri-O-benzyl-alpha-L-C-fucopyranoside)-1-propene (1) (4.04 g, 7.96 mmole, 3.00 mmole equiv.) is added dropwise in anhydrous tetrahydrofuran (17.5 mL) and gently refluxed for 6 hours. After 6 hours at reflux, the reaction is terminated by the careful addition of 50% methanol in toluene (5 mL) at 0° C. and then 4M hydrochloric acid until the pH is 1–2 and the reaction contents are diluted with ethyl acetate. The heterogeneous layers are separated and the organic phase is washed twice with portions of 1.0M hydrochloric acid, saturated sodium thiosulfite and brine. The crude product is dried over anhydrous sodium sulfate, filtered and plugged through a small pad of silica gel and eluted with ethyl acetate. The solvent is removed in vacuo which afforded an oil that is chromatographed on Baker grade flash silica gel (47–61 mm) (ratio 50 to 1) and eluted with 10% ethyl acetate in hexane, 50% ethyl acetate in hexane, 100% ethyl acetate. Concentration in vacuo afforded 2-(tri-O-benzyl-alpha-L-C-methylfucopyranose)-3-[3-O-(Lithocholic acid)]-1-propene (2) as a white foam powder.

Example 3

Preparation of 1-[3-O-(Lithocholic acid)]-2-(alpha-L-C-methylfucopyranose)-propane (3).

The following compound is prepared as follows.

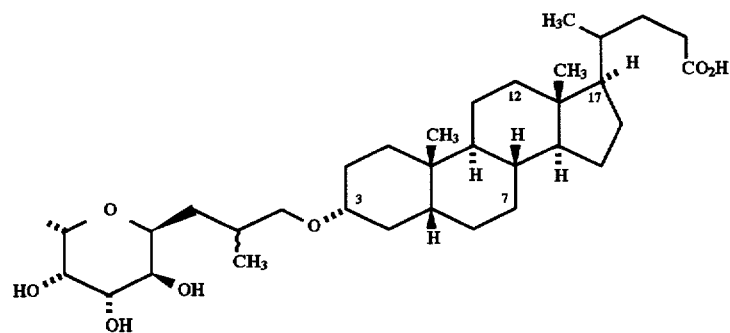

2-(tri-O-benzyl-alpha-L-C-methylfucopyranose)-3-[3-O-(Lithocholic acid)]-1-propene (2) (520 mg, 0.877 mmole, 1.00 mmole equiv.) is dissolved in 10% acetic acid in methanol (8.8 mL, 0.1M), 5% or 10% palladium on carbon (35 mg per mmole of substrate wetted with toluene) and placed on a Parr hydrogenation apparatus. The reaction vessile is evacuated and re-filled with hydrogen thrice and then shaken at 50 PSI for 48 hours (see note in general experimental above). The reaction is terminated by filtering the contents through Celite to remove the catalyst. The filtered solution was concentrated in vacuo and washed with dichloromethane to afford 332 mg of 1-[3-O-(Lithocholic acid)]-2-(alpha-L-C-methylfucopyranose)-propane (3) as a white powder.

Example 4

Preparation of 1-[3-O-(Lithocholic acid)]-2-(tri-O-benzyl-alpha-L-C-methyl-fucopyranose)-2', 3'-propanediol (4).

The following compound is prepared as follows.

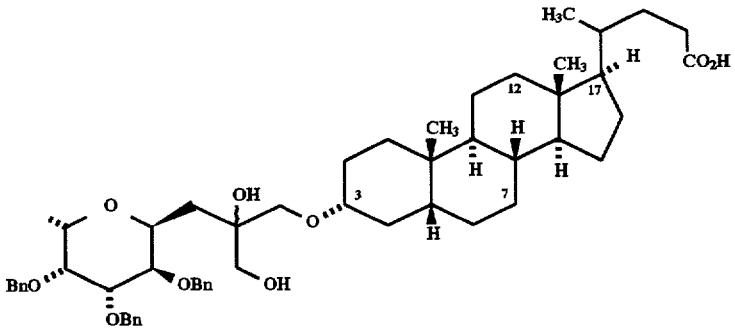

To a solution of 2-(tri-O-benzyl-alpha-L-C-methylfucopyranose)-3-[3-O-(Lithocholic acid)]-1-propene (2) (1.00 g, 1.18 mmole, 1.00 mmole equiv.) in anhydrous dichloromethane (5.9 mL, 0.2M) at ambient temperature is added osmium tetroxide (0.118 mmole, 23.6 mL of a 0.5M solution in toluene, 0.10 mmole equiv.) and N-methylmorpholine-N-oxide (1.38 g, 11.8 mmole, 10.00 mmole eqiv.). The reaction contents are stirred at ambient temperature for 6 days and the reaction is terminated by the addition of 25% aqueous sodium metasulfite and stirred for 1 hour. The heterogeneous layers are separated and the organic phase is washed twice with portions of 25% aqueous sodium metasulfite, 1.0M hydrochloric acid, sodium bicarbonate and brine. The crude product is dried over anhydrous sodium sulfate, filtered and plugged through a small pad of silica gel. The solvent is removed in vacuo which afforded an oil that is chromatographed on Baker grade flash silica gel (47–61 mm) (ratio of 50 to 1) and eluted with 5% then 10% methanol in chloroform. Concentration in vacuo afforded 728 mg of 1-[3-O-(Lithocholic acid)]-2-(tri-O-benzyl-alpha-L-C-methyl-fucopyranose)-2', 3'-propanediol (4), 70–81%.

Example 5

Preparation of 1-[3-O-(Lithocholic acid)]-2-(alpha-L-C-methylfucopyranose)-2',3'-propanediol methyl ester (5).

The following compound was prepared as follows.

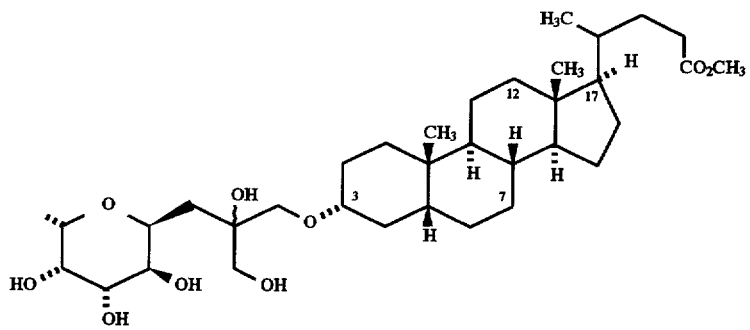

1-[3-O-(Lithocholic acid)]-2-(tri-O-benzyl-alpha-L-C-methylfucopyranose)-2', 3'-propanediol (4) (353 mg, 0.40 mmole, 1.00 mmole equiv.) is dissolved in 10% acetic acid in methanol (10 mL, 0.2M), 10% palladium on carbon is added (35 mg per mmole of substrate wetted with toluene) and the solution is placed on a Parr hydrogenation apparatus. The reaction vessile is evacuated and re-filled with hydrogen thrice and then shaken at 50 PSI for 48 hours. The reaction is terminated by filtering the contents through Celite to remove the catalyst. Concentration in vacuo and re-evaporation in 10% acetic acid in methanol afforded 1-[3-O-(Lithocholic acid)]-2-(alpha-L-C-methylfucopyranose)-2', 3'-propanediol methyl ester 220 mg (5) as a white powder. 88%.

Example 6

Preparation of 1[-3-O-(Lithocholic acid)]-2-(alpha-L-C-methylfucopyranose)-propane trisulfate (6).

The following compound would be prepared as follows

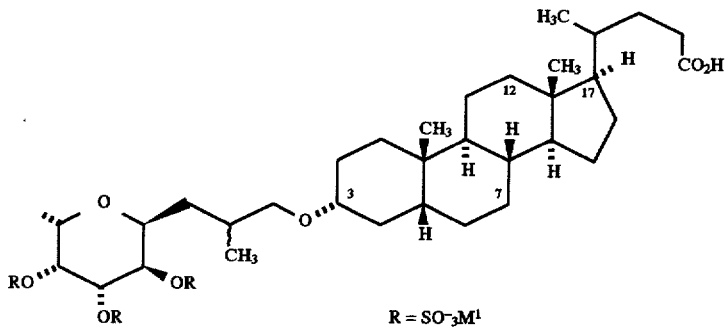

$R = SO_3M^1$

To a solution of 1-[3-O-(Lithocholic acid)]-2-(alpha-L-C-methylfucopyranose)-propane (5) (50 mg, 84.3 mmole, 1.00 mmole equiv.) in anhydrous dimethylformamide (4.2 mL, 0.2M) at ambient temperature is added sulfur trioxide pyridine complex polymer bound (843 mmole, 10 mmole equiv.). The reaction contents are stirred at ambient temperature and then warmed to a gentle reflux for 8 hours. The reaction is cooled to ambient temperature and terminated by the addition of sodium carbonate with filtering the polymer through celite and flushed with methanol. The solvent is removed in vacuo affording an oil that is azeotrophed with toluene. Concentration in vacuo afforded 1-[3-O-Lithocholic acid)]-2-alpha-L-C-methylfucopyranose)-propane trisulfate (6) which is then desalted using standard conditions. Reference: Graf, W. Chem. Ind. 1987, 232.

An alternate procedure to prepare 1-[3-O-(Lithocholic acid)]-2-alpha-L-C-methylfucopyranose)-propane trisulfate (6) is as follows. To a solution of 1-[3-O-(Lithocholic acid)]-2-(alpha-L-C-methylfucopyranose)-propane(5)(50 mg, 84.3 mmole, 1.00 mmole equiv,) in anhydrous dimethylformamide (4.2 mL, 0.2M) at ambient temperature is added sulfur trioxide pyridine complex (843 mmole, 10 mmole equiv.). The reaction contents are stirred at ambient temperature and then warmed to a gentle reflux for 8 hours. The reaction is cooled to ambient temperature and terminated by the addition of sodium carbonate with filtering through celite and flushed with methanol. The solvent is removed in vacuo affords an oil that is azeotrophed with toluene. Concentration in vacuo affords 1-[3-O-(Lithocholic acid)]-2-(alpha-L-C-methylfucopyranose)-propan trisulfate (6) which is then desalted using standard conditions.

Example 7

Preparation of 1-[3-O-(Lithocholic acid)]-2-oxo-2-(tri-O-benzyl-alpha-L-C-methylfucopyranose)-ethane (7).

The following compound would be prepared as follows:

1.00 mmole equiv.) in anhydrous dichloromethane (0.337 mL, 0.2M) at −78° C. is added excess ozone. The reaction contents are stirred at −78° C. for 1 hour and the reaction is terminated by the addition of dimethylsulfide (30.7, 26.8 mg, 0.416 mmole, 10 mmole equiv.) and stirred for 1 hour and allowed to warm to ambient temperature. Water is added and the heterogeneous layers are separated and the organic phase is washed twice with portions of 1.0M hydrochloric acid, sodium bicarbonate and brine. The crude product is dried over anhydrous sodium sulfate, filtered and plugged through a small pad of silica gel. The solvent is removed in vacuo which affords an oil that is plugged on Baker grade flash silica gel (47–61 mm) (ration of 50 to 1) and eluted with 50% ethyl acetate in hexane. Concentration in vacuo affords 1-[3-O-(Lithocholic acid)]-2-oxo-2-(tri-O-benzyl-alpha-L-C-methylfucopyranose)-ethane (7).

Example 8

Preparation of 1-[3-O-(Lithocholic acid)]-2-oxo-2-(alpha-L-C-methylfucopyranose)-ethane (8).

The following compound is prepared as described.

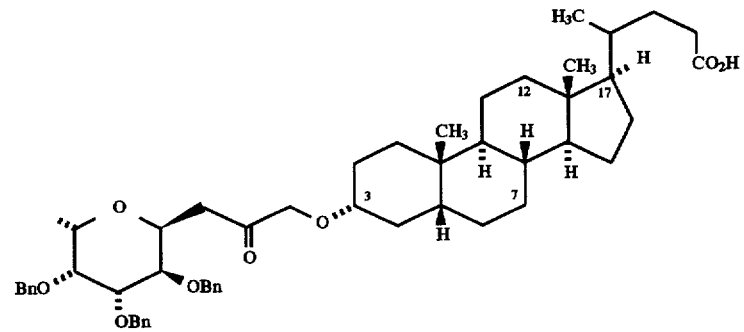

To a solution of 2-[3-O-(Lithocholic acid)]-3-(C-tri-O-benzyl-L-fucopyranose)-1-propene (40 mg, 0.067 mmole,

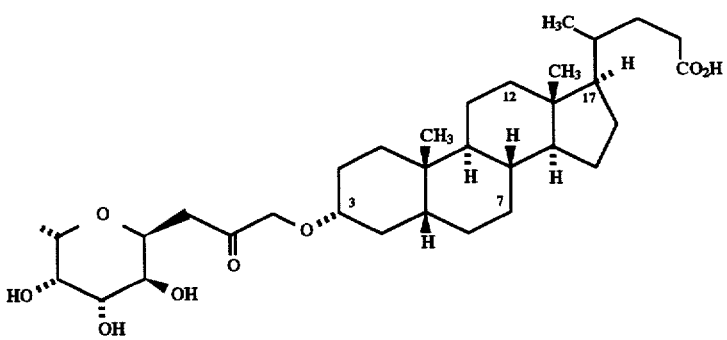

1-[3-O-(Lithocholic acid)]-2-oxo-2-(tri-O-benzyl-alpha-L-C-methylfucopyranose)-ethane (7) (15 mg, 0.0253 mmole, 1.00 mmole equiv.) is dissolved in 10% acetic acid in methanol (ethyl acetate can be added to enhance solubility), 5% or 10% palladium on carbon is added (35 mg per mmole of substrate, wetted with toluene) and placed on a Parr hydrogenation apparatus. The reaction vessile is evacuated and re-filled with hydrogen thrice and then shaken at 5 PSI for 24 to 48 hours. The reaction is terminated by filtering the contents through Celite to remove the catalyst. The filtered solution is concentrated in vacuo and washed with dichloromethane to give 1-[3-O-(Lithocholic acid)]-2-oxo-2-(alpha-L-C-methylfucopyranose)-ethane (8).

Example 9

1-[3-O-(Lithocholic acid)]-2-hydroxy-2-(tri-O-benzyl-alpha-L-C-methylfucopyranose)-ethane (9).

The following compound would be prepared as described.

Example 10

1-[3-O-(Lithocholic acid)]-2-hydroxy-2-(alpha-L-C-methyl-fucopyranose)-ethane (10).

The following compound would be prepared as described.

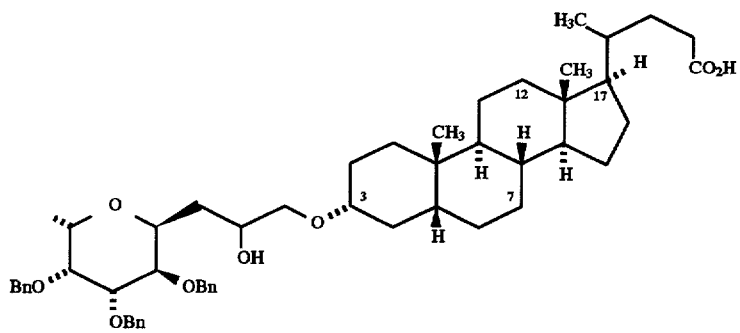

1-[3-O-(Lithocholic acid)]-2-oxo-2-(alpha-L-C-methylfucopyranose)-ethane (8) can be reduced under standard conditions with either R-Alpine-Borane (CAS [64081-12-5]) or S-Alpine-Borane (CAS [100013-07-8]) according

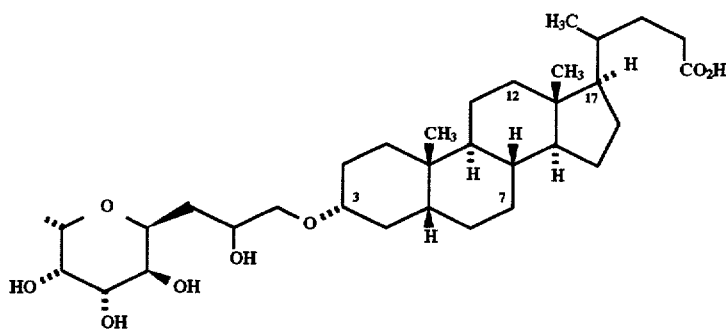

to literature procedures. *J. Ore. Chem.* (1977), 42:2534. 1-[3-O-(Lithocholic acid)]-2-hydroxy-2-(tri-O-benzyl-alpha-L-C-methylfucopyranose)-ethane (9). Additional References: Miyano, M., Stealy, M. A., Chem. Commun., (1973), 180. Schaub, R. E., Weiss, M. J., Tetrahedron Lett., (1973), 129. Gnudzinskas, C. V., Weiss, M. J., Tetrahedron Lett., (1973), 141.

1-[3-O-(Lithocholic acid)]-2-hydroxy-2-(tri-O-benzyl-alpha-L-C-methylfucopyranose)-ethane (7) (15 mg, 0.0253 mmole, 1.00 mmole equiv.) is dissolved in 10% acetic acid in methanol (ethyl acetate can be added to enhance solubility), 5% or 10% palladium on carbon is added (35 mg per mmol. of substrate, wetted with toluene) and placed on a parr hydrogenation apparatus. The reaction vessile is evacuated and re-filled with hydrogen thrice and then shaken at 50 PSI for 24 to 48 hours. The reaction is terminated by filtering the contents through Celite to remove the catalyst. The filtered solution is concentrated in vacuo and washed with dichloromethane to give 1-[Lithocholic acid)]-2-hydroxy-2-(alpha-L-C-methylfucopyranose)-ethane (10).

Example 11

The following compound was prepared as described (11).

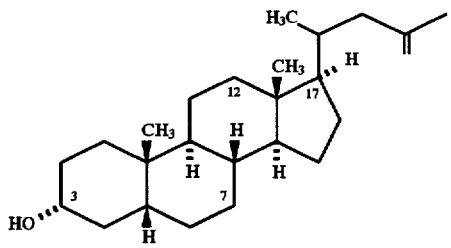

and the following compound was prepared as described (12).

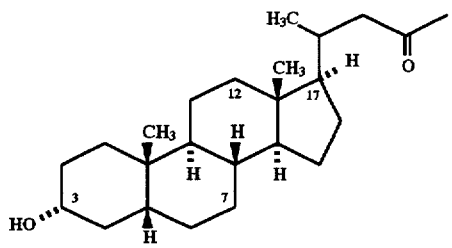

To a solution of lithocholic acid methyl ester (1.0 g, 2.56 mmole, 1.00 mmole eqiv.) in anhydrous THF (12.8 mL, 0.2M) at 0° C. was added trimethylsilylmethyl lithium (10.24 mL, 10.24 mmole, 4.00 mmole eqiv. in 1.0M in pentane). The reaction contents stirred at 0° C. for and then allowed to warm to ambient temperature and stirred for 12 hours. After 12 hours, the reaction was terminated by the careful addition of trimethylsilyl chloride (1.11 gm, 10.24 mmole, 1.3 mL, 4.00 mmole equiv.) and stirred for 6 hours. The reacton contents were diluted with ethyl acetate and the contents poured slowly into water. The heterogeneous layers were separated and the organic phase was washed twice with portions of water, 1.0M hydrochloric acid and brine. The crude product was dried over anhydrous sodium sulfate, filtered and plugged through a small pad of silica gel. The solvent was removed in vacuo which afforded an oil that was chromatographed on Baker grade flash silica gel (47–61 mm) (ratio of 50 to 1) and eluted with 1% then 5% ethyl acetate in hexanes. Concentration in vacuo afforded an upper Rf material 375 mg (alkene) and a lower Rf material 500 mg (ketone). Overall recovery was 85% for the alkene and ketone.

For the conversion of carboxylic acid derivatives into allylsilanes see: Anderson, M. B,; Fuchs, P. L. *Synthetic Commun.* (1987), 17: 621.

Example 12

Anti-inflammatory Effects

Using the arachidonic acid (AA), murine skin inflammation model, described by Harris, R. R. et al. (Skin Pharmacol 1990; 3:29–40) the anti-inflammatory activity of (5) was tested. For comparison, Lithocholic acid and Methyl lithocholate, were also tested. Compounds were dissolved at 100 mg/mL in $CHCl_3$, except for lithocholic acid which was dissolved in $CHCl_3$:$CH_3OH$ (1:1); 10 uL of each compound was applied to the ear immediately following arachidonic acid (AA). AA was applied alone, or followed immediately with methyl lithocholate, ketone (12) alkene (11) or compound (5). 90 minutes later, a 6 mm disk of each ear was removed and weighed. The results are shown in Table 1. Briefly, it was observed that the percent inhibition of swelling caused by AA alone was reduced by about 48.5% for compound (5), about 17.5% for Methlylithocholate acid and 22.5% for Lithocholic acid.

TABLE 1

Anti-Inflammatory Activities
Topical Administration in Arachidonic Acid Ear Model
(Average of two experiments).

| Compound | % Inhibition of Swelling | Amount Applied |
|---|---|---|
| methyl lithocholate | 17.5% | 1 mg (2.6 umole) |
| Ketone, (12) | 22.5% | 1 mg (2.6 umole) |
| Lithocholic acid | 30.5% | 1 mg (2.6 umole) |
| Alkene (11) | 40.0% | 1 mg (2.6 umole) |
| (5) | 48.5% | 1 mg (1.6 umole) |

The instant invention is shown and described herein in what is considered to be the most practical, and preferred embodiments. It is recognized, however, that departures may be made therefrom which are within the scope of the invention, and that obvious modifications will occur to one skilled in the art upon reading this disclosure.

The present invention is not to be limited in scope by the exemplified embodiments which are intended as illustrations of single aspects of the invention, and any chemical compound or method which are equivalent are within the scope of the invention. Indeed, various modifications of the invention in addition to those described herein will become apparent to those skilled in the art from the foregoing description and accompanying drawings. Such modifications are intended to fall within the scope of the appended claims.

What is claimed is:

1. A compound having the formula:

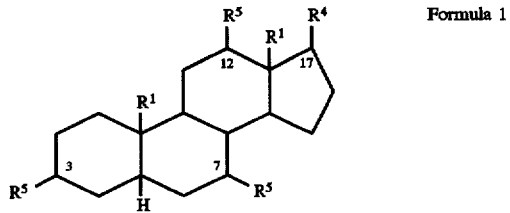

Formula 1 wherein:

$R^1$ is selected from the group consisting of H, and lower alkyl;

$R^4$ is selected from the group consisting of C1–C8 alkyl, C2–C10 alkene, —$CH(CH_3)$—$(CH_2)_n$—COD and —$CH(CH_3)$—$(CH_2)_n COR^5$;

wherein D is selected from the group consisting of $OR^1$, $NR_2^1$, and O—$M^1$;

at least one $R^5$ is

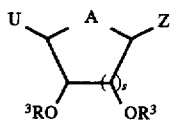

and the remaining $R^5$s are selected from the group consisting of $R^1$, oxo, —$OSO_3M^1$, —$SO_3M^1$, and O-carbohydrate;

Z is selected from the group consisting of —$CH_2WCH_2J$, —C≡$CCH_2J$, =C=$CHCH_2J$, —$ArCH_2J$, and —$(CH_2)_nJ$, wherein J is bound to the steroid and J is oxygen, sulfur, or nitrogen;

W is selected from the group consisting of C=O, C=$CR_2^1$, $CR^1CR_3^1$, $CR^1$—$CR_2^1OR^1$, $COR^1$—$CR_2^1OR^1$, $CR_2^1$, $CR_2$—$CR_2^2OR^3$, and $CR_2$—$CR^2R_2^1$;

n is a positive integer;

$M^1$ is a $Na^+$, $K^+$, $Mg^{++}$, or $Ca^{++}$ion;

$R^2$ is selected from the group consisting of $OR^1$, $NR_2^1$, and $SR^1$;

$R^3$ is selected from the group consisting of $R^1$, $SO_3M^1$, and O-carbohydrate;

s is 1, 2,or 3;

U is selected from the group consisting of $CH_3$, $CH_2OR^1$, $CH_2O$-protecting group, $CH_2OSO_3M^1$, $CH_2SO_3M^1$, $CH_2OR^3$, and COD; and A is selected from the group consisting of O, S, $NR_2^1CR_2^1$, and $NR^1$.

2. The compound:

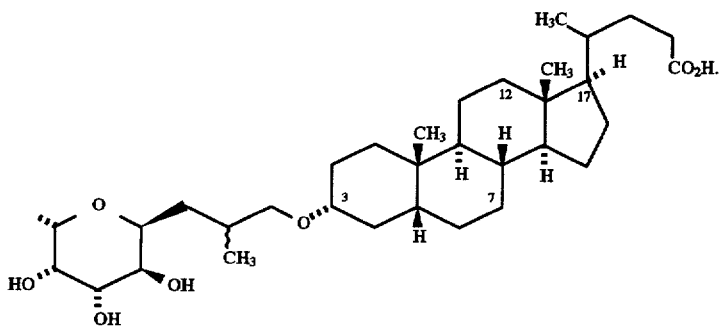

3. The compound:

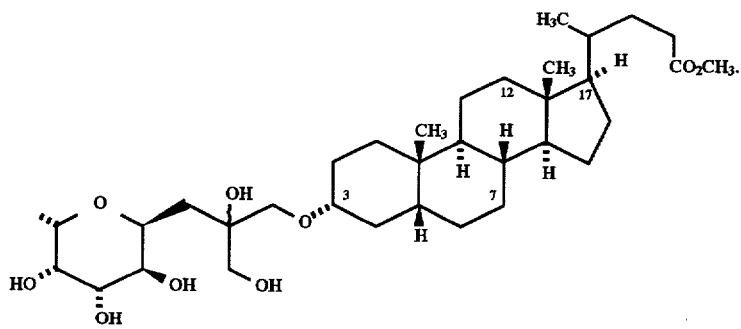

4. The compound:
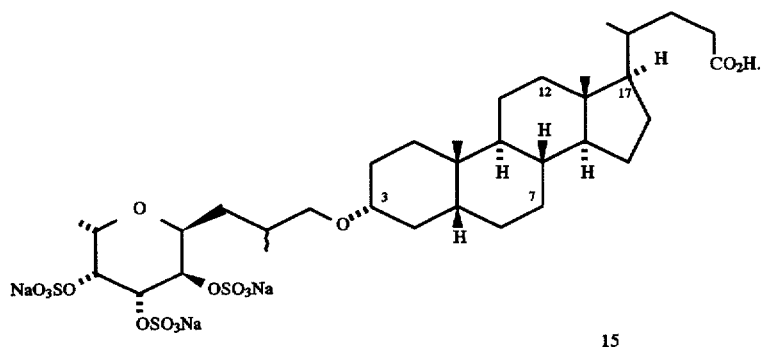
5. The compound:
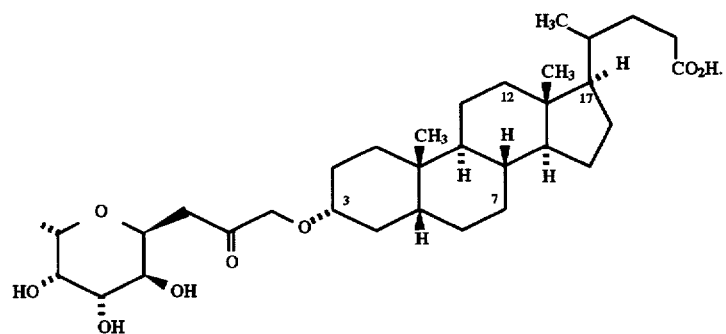
6. The compound:
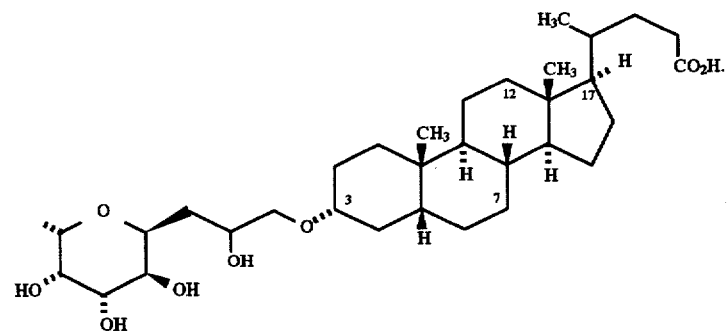
7. A pharmaceutical composition, comprising a pharmaceutically acceptable excipient carrier and a therapeutically effective amount of a compound of claim 1.
8. A pharmaceutical composition as in claim 7 wherein the compound is:

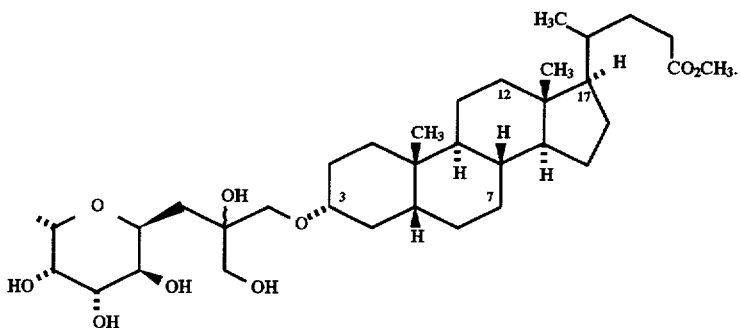

9. A method of treating inflammation in a subject in need thereof, comprising the step of administering to the subject a therapeutically effective amount of the compound of claim 1.

10. A method of treating inflammation as in claim 9 wherein the compound is:

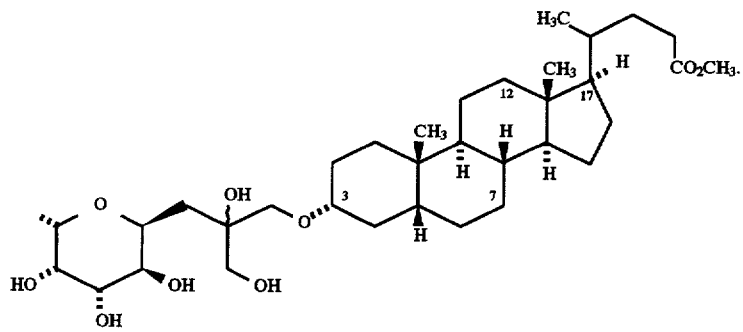

11. A method of determining a site of inflammation in a patient, comprising the steps of:
   administering to the patient a compound of claim 1, wherein a detectable label is attached to the compound;
   allowing the labelled compound sufficient time to circulate in the patient; and
   detecting the location of the labelled compound in the patient, whereby the site of inflammation is determined.

12. A method of determining a site of inflammation as in claim 11 wherein the compound is:

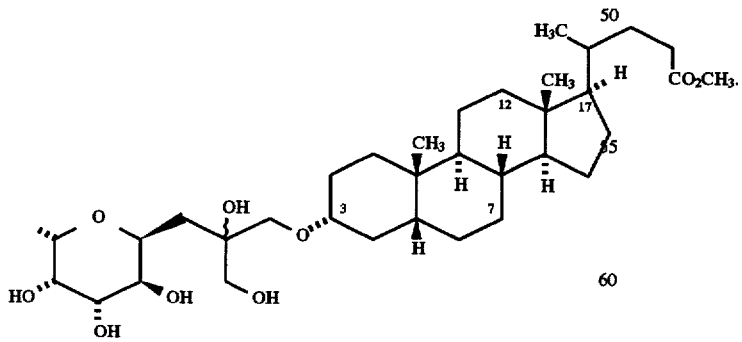

13. A method of determining a site of inflammation as in claim 11, wherein the detectable label is a radioactive label.

14. A compound as in claim 1 wherein $R^4$ is 2,6-dimethylexyl.

15. A compound as in claim 1 wherein $R^4$ is 2,6-dimethyl-3-ethyl-hex-4-enyl.

* * * * *